(12) United States Patent
Kettle

(10) Patent No.: US 7,108,997 B2
(45) Date of Patent: Sep. 19, 2006

(54) ASSAY FOR DETECTING INHIBITORS OF THE ENZYME MYELOPEROXIDASE

(75) Inventor: Anthony Kettle, Christchurch (NZ)

(73) Assignee: AstraZeneca AB, Sodertalje (SE)

( * ) Notice: Subject to any disclaimer, the term of this patent is extended or adjusted under 35 U.S.C. 154(b) by 277 days.

(21) Appl. No.: 10/476,999

(22) PCT Filed: May 6, 2002

(86) PCT No.: PCT/SE02/00877

§ 371 (c)(1), (2), (4) Date: Nov. 6, 2003

(87) PCT Pub. No.: WO02/090575

PCT Pub. Date: Nov. 14, 2002

(65) Prior Publication Data

US 2004/0142407 A1 Jul. 22, 2004

(30) Foreign Application Priority Data

May 8, 2001 (WO) ............... PCT/SE01/01014
Nov. 9, 2001 (SE) .......................... 0103766

(51) Int. Cl.
*C12Q 1/28* (2006.01)
(52) U.S. Cl. ........................................ 435/28
(58) Field of Classification Search .............. 435/28
See application file for complete search history.

(56) References Cited

U.S. PATENT DOCUMENTS

| 5,976,823 | A | 11/1999 | Wu | |
|---|---|---|---|---|
| 6,046,019 | A * | 4/2000 | Goumeniouk et al. | 435/28 |
| 2004/0022871 | A1* | 2/2004 | Mainnemare | 424/661 |
| 2004/0029871 | A1* | 2/2004 | Thong et al. | 514/222.8 |

OTHER PUBLICATIONS

Hope et al., "Large-Scale Purification of Myeloperoxidase from HL60 Promyelocytic Cells: Characterization and Comparison to Human Neutrophil Myeloperoxidase", Protein Expression and Purification 18, 269-276 (2000).
Suzuki et al., "Assay Method for Myeloperoxidase in Human Polymorphonuclear Leukocytes", Anal. Biochem. 132, 345-352 (1983).
Bozeman et al., "Inhibition of the Human Leukocyte Enzymes Myeloperoxidase and Eosinophil Peroxidase by Dapsone", Biochem. Pharmacol. 44, 553-563 (1992).
Akbiyik et al., "In vitro and in vivo inhibition of myeloperoxidase with 5-fluorouracil," Eur. J. Clin. Pharmacol. 57, 631-636 (2001).
Kettle et al., "Assessing Molecular, Cell and Tissue Damage", Methods Enzymol. 244, 502-512 (1994).
Grisham et al., "Assessment of Leukocyte Involvement during Ischemia and Reperfusion of Intestine", Methods Enzymol. 186, 729-742 (1990).

* cited by examiner

*Primary Examiner*—Ralph Gitomer
(74) *Attorney, Agent, or Firm*—Karen H. Kondrad

(57) ABSTRACT

The invention is an assay for detecting inhibitors of the enzyme myeloperoxdase The assay method comprises reacting myeloperoxdase with hydrogen peroxide and a chloride source to generate hypochlorous acid in the presence of a potential inhibitor of said myeloperoxidase; reacting any formed hypochlorous acid with an amine to form the corresponding chloramino; optionally removing any unreacted hydrogen peroxide; reacting any for-med chloramine with a detector compound in the presence of iodide to form oxidized detector compound; determining the amount of formed oxidized detector compound by measuring the absorbents or fluorescence at a suitable wavelength; and identifying as inhibitors of myeloperoxidase those compounds which cause the amount of formed oxidized detector compound to be decreased The assay is useful in diagnostic tests for myeloperoxidase activity.

6 Claims, 3 Drawing Sheets

ASSAY FOR DETECTING INHIBITORS OF THE ENZYME MYELOPEROXIDASE

Figure 1:
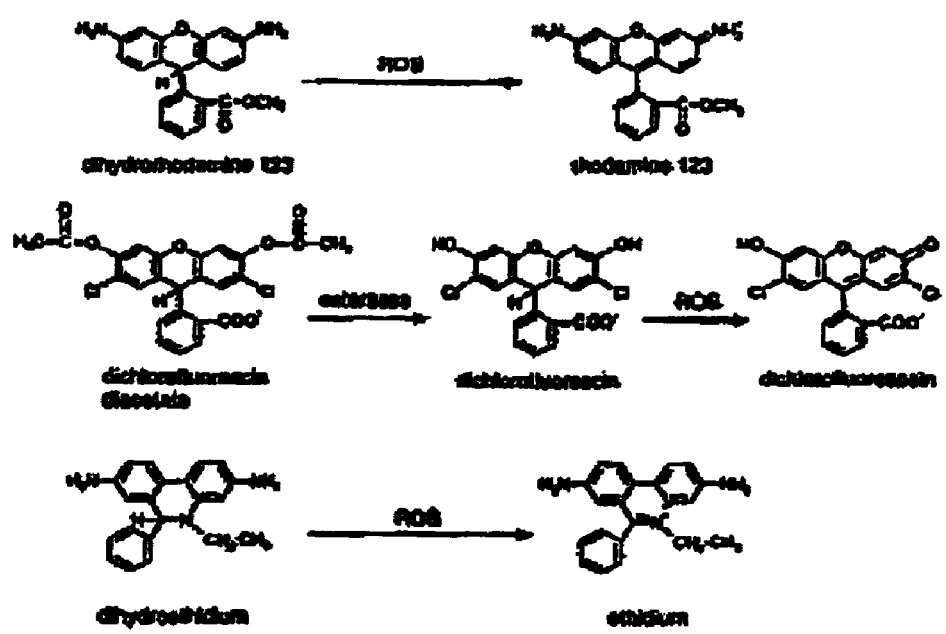

This application is a National Stage application filed under Rule 371 based on PCT/SE02/00877 filed May, 6, 2002, which claims priority to Sweden application 0103766-2 filed Nov. 09, 2001, which claims priority to Sweden PCT/SE01/01014 filed May 8, 2001.

BACKGROUND OF THE INVENTION

Resistance to infection by microorganisms involves both non-specific mechanisms and adaptive immune responses mediated by B and T lymphocytes. Non-specific mechanisms such as enzyme action, pH and epithelial tissue secretions prevent invasion by many organisms. However, when the first line of defense is breached, phagocytes engulf infectious agents and process them leading to the stimulation of B and T cells. Deficiencies in the phagocytic system, whether hereditary or acquired, have serious consequences, since microorganisms with low pathogenicity for normal individuals can cause recurrent infections in individuals with ineffective phagocytic systems.

Polymorphonuclear leukocytes (PMNs) are of particular importance for combating infections. These cells contain an enzyme, myeloperoxidase, with well documented microbicidal action. PMNs act non-specifically by phagocytosis to engulf microorganisms, incorporate them into vacuoles, termed phagosomes, which fuse with granules containing myeloperoxidase to form phagolysosomes. In phagolysosomes the enzymatic activity of the myeloperoxidase leads to the formation (from hydrogen peroxide and chloride) of hypochlorous acid, a potent bactericidal compound. Hypochlorous acid is oxidizing in itself, and reacts most avidly with thiols and thioethers but also converts amines into chloramines and chlorinates aromatic amino acids. Macrophages are large phagocytic cells which, like PMNs are capable of phagocytosing microorganisms. Macrophages can generate hydrogen peroxide and upon activation also produce myeloperoxidase. In addition, myeloperoxidase in the plasma is taken up by macrophages.

Linkage of myeloperoxidase activity to disease has been implicated in numerous inflammatory diseases including Alzheimer's disease, multiple sclerosis, asthma, atherosclerosis, cancer, cystic fibrosis, chronic obstructive pulmonary disease, inflammatory bowel disease, and rheumatoid arthritis. Assays for identification of inhibitors of myeloperoxidase will be invaluable in demonstrating the contribution of hypochlorous acid to the pathogenesis of such diseases, as well as for diagnostic tools. They will also provide the platform for the development of effective drugs against myeloperoxidase-dependent tissue damage. A suitable screening assay for MPO inhibitors should measure the chlorination activity of myeloperoxidase under realistic physiological conditions. It must be simple, sensitive, and produce a coloured or fluorescent product, and it must not perturb the activity of MPO. The detector will need to be present at high enough concentrations to scavenge all the hypochlorous acid produced but not so as to react directly with the enzyme. Currently, the most commonly used assay is based on the primary formation of taurine chloramine from hypochlorous acid and taurine. Previous attempts to use modified forms of this taurine chloramine assay for measuring the activity of myeloperoxidase have revealed specific problems that negate its use for screening potential inhibitors of the enzyme. Major problems are that dimethylsulphoxide (DMSO), the solvent in which test compounds are most conveniently and usually dissolved, interferes with the assay, and many of the test compounds absorb in the same region as the commonly used chromophore.

Physiologically, PMN-derived myeloperoxidase primarily catalyzes the hydrogen peroxide-dependent oxidation of halides such as chloride ions, but its ability to use electron donors such as O-dianisidine as a substrate forms the basis of an assay to quantify PMNs in inflamed tissue. Adaptations of the method to avoid artifacts caused by tissue/blood constituents, such as the cytosolic enzymes, catalase and glutathione peroxidase, reducing substrates such as glutathione and ascorbic acid, and heme proteins have been described (Grisham et al., Methods in Enzymology, Vol. 186, Ed. Packer et al., San Diego: Academic Press, pp. 729–742 (1990)). However, there is a need for a more reliable analytical method of quantifying the PMN content of inflamed tissues that is not affected by other endogenous tissue constituents.

The present invention describes a simple, sensitive and robust assay that avoids the major problems associated with currently known assays and that is well suited to the identification of inhibitors of myeloperoxidase. In another aspect, the present invention is useful for certain diagnostic tests associated with myeloperoxidase.

DESCRIPTION OF THE INVENTION

In a first aspect, the present invention provides a method for identifying inhibitors of myeloperoxidase (MPO), the method comprising:
  reacting myeloperoxidase with hydrogen peroxide and a chloride source to generate hypochlorous acid in the presence of a potential inhibitor of said myeloperoxidase;
  reacting any formed hypochlorous acid with a suitable amine to form the corresponding chloramine;
  optionally removing any unreacted hydrogen peroxide;
  reacting any formed chloramine with a suitable detector molecule in the presence of iodide to form oxidised detector molecule;
  determining the amount of formed oxidised detector molecule by measuring the absorbance or fluorescence at a suitable wavelength;
  identifying as inhibitors of myeloperoxidase those compounds which cause the amount of formed oxidised detector molecule to be decreased.

In one embodiment of the above invention, the amine used is taurine which is converted by hypochlorous acid into taurine chloramine. A suitable concentration of taurine is about 5 to 10 mM.

In another embodiment, any unreacted hydrogen peroxide is removed using catalase. A suitable concentration of catalase is about 10 to 20 µM.

Sodium chloride may be used as a suitable source of chloride, for example, in an amount of about 50 to 150 mM.

Hydrogen peroxide may be added as such, or may be generated in situ using, for example, enzymatic generation of hydrogen peroxide by an oxidase such as glucose oxidase or xanthine oxidase. A suitable concentration of hydrogen peroxide is, for example, 10 to 100 µM.

In another embodiment, the detector molecule used is a benzidine derivative. A preferred benzidine derivative is 3,3',5,5'-tetramethylbenzidine (TMB), and the formed oxidised 3,3',5,5'-tetramethylbenzidine is assayed by measuring the absorbance at 645 to 650 nM.

In alternative embodiments, the detector molecule is a fluorescent probe such as one of the molecules shown in FIG. 1.

For example, dihydrorhodamine may be used as the detector molecule. This non-fluorescent compound is oxidized to rhodamine, which emits fluorescence at 536 nm when excited at 500 nm.

reacting myeloperoxidase with hydrogen peroxide to generate hypochlorous acid in the presence of a potential myeloperoxidase inhibitor and reacting any formed hypochlorous acid with taurine to form taurine chloramine in a suitable buffer containing sodium chloride and 10 mM taurine;

optionally adding catalase to a concentration of up to about 20 µg/mL to destroy any residual hydrogen peroxide;

reacting any formed taurine chloramine with 3,3',5,5'-tetramethylbenzidine in the presence of potassium iodide to form oxidised 3,3',5,5'-tetramethylbenzidine in a suitable buffer containing 3,3',5,5'-tetramethylbenzidine and 10 to 20% dimethylformamide; and measuring the amount of formed oxidised 3,3',5,5'-tetramethylbenzidine.

Buffers that may be used include suitable acetate, citrate or phosphate buffers of pH 5 to pH 8. The buffer should be present at a concentration of at least 10 mM, preferably at least 20 mM. Preferably the reaction with potassium iodide is performed at about pH 5.4

Thus, in one particular embodiment, the method of the present invention comprises:

reacting myeloperoxidase (2.5 nM) with hydrogen peroxide (100 µM) and sodium chloride (140 mM) in 20 mM phosphate buffer pH 6.5 to generate hypochlorous acid in the presence of a potential myeloperoxidase inhibitor (in compound solvent, DMSO, at 1%) and reacting any formed hypochlorous acid with 10 mM taurine to form taurine chloramine;

stopping and developing the assay by adding, as final concentrations, glacial acetic acid (400 mM), potassium iodide (100 µM) and 3,3',5,5'-tetramethylbenzidine in dimethylformamide (10 mM); and measuring the amount of formed oxidised 3,3',5,5'-tetramethylbenzidine.

In another particular embodiment, the method of the present invention comprises:

reacting myeloperoxidase (5 to 20 nM) with hydrogen peroxide (100 µM) to generate hypochlorous acid in the presence of a potential myeloperoxidase inhibitor and reacting any formed hypochlorous acid with taurine to form taurine chloramine in 20 mM pH 6.5 phosphate buffer containing 100 mM sodium chloride and 10 mM taurine;

adding catalase to a concentration of 20 µg/mL to destroy any residual hydrogen peroxide;

reacting any formed taurine chloramine with 3,3',5,5'-tetramethylbenzidine in the presence of 200 µM potassium iodide to form oxidised 3,3',5,5'-tetramethylbenzidine in 200 mM sodium acetate buffer pH 5.4 containing 2 mM 3,3',5,5'-tetramethylbenzidine, and 10 to 20% dimethylformamide; and measuring the amount of formed oxidised 3,3',5,5'-tetramethylbenzidine.

In another particular embodiment, the method of the present invention comprises:

reacting myeloperoxidase (2.7 nM) with hydrogen peroxide (50 µM) in 20 mM phosphate buffer pH 6.5 containing 140 mM sodium chloride and 10 mM taurine in the presence of a potential myeloperoxidase inhibitor; this assay solution (150 µL) was then added to each well of a 96 well plate;

stopping and developing the reaction by adding to each well 50 µL of a reagent comprising sodium iodide (100 µM), acetic acid (400 mM) and 10 mM TMB in 50% dimethylformamide; and measuring the amount of formed oxidised 3,3',5,5'-tetramethylbenzidine.

In another particular embodiment, the method of the present invention uses an assay buffer comprising 20 mM sodium/potassium phosphate buffer pH 6.5 containing 10 mM taurine and 100 mM NaCl, and a developing reagent comprising 2 mM TMB, 200 µM KI, 200 mM acetate buffer pH 5.4 with 20% DMF.

Further particular embodiments are described in the Examples section below.

The present invention overcomes two specific problems that precluded use of known taurine chloramine assays for measuring the activity of myeloperoxidase as a way of screening for potential enzyme inhibitors. Firstly, a commonly used solvent, dimethylsulphoxide, interfered with these assays, and, secondly, many test compounds absorbed optically in the same region as the chromophore.

The present invention is a modified taurine chloramine assay in which the interference by dimethylsulphoxide is minimized and the detection process is free of optical interference by test compounds.

Inhibition of purified myeloperoxidase by test compounds has been measured using the modified assay establishing that the modified assay is useful for assessing the ability of compounds to inhibit myeloperoxidase. Further, the present invention meets the requirements necessary for high-throughput screening (HTS). Still further, the invention provides a method for detecting inhibitors of myeloperoxidase useful for identifying compounds with potential for treating subjects suffering from diseases in which MPO activity is implicated.

It has been found that oxidation of a suitable detector molecule such as 3,3',5,5'-tetramethylbenzidine by taurine chloramine catalysed by iodide at a suitable pH provides an assay which suffers from minimal interference by dimethylsulphoxide (DMSO). When the detector molecule is 3,3',5,5'-tetramethylbenzidine, a blue product is formed having an absorbance maximum at about 645 nm.

The assay of the present invention is a sensitive and specific method for detecting hypochlorous acid, HOCl. It is also useful for determining the ability of test compounds to inhibit myeloperoxidase. It is particularly useful for HTS to identify inhibitors of myeloperoxidase.

For the particular embodiment disclosed in Example 3 below, it has been found that 20 mM pH 6.5 phosphate buffer containing 100 mM sodium chloride and 10 mM taurine ($RNH_2$) (hereinafter PBST) minimizes the inhibition of myeloperoxidase by hydrogen peroxide, and a concentration of taurine of 10 mM has been found to be sufficient to ensure that all hypochlorous acid (HOCl) generated (see Reaction 1, below) is trapped as taurine chloramine (RN-HCl) (see Reaction 2, below). Taurine chloramine has been found to be stable at room temperature for at least an hour. Therefore, to minimize potential consumption of taurine chloramine by reaction with test compounds, the assay has been designed so that the amount generated is about 5–10 times greater than the concentration of the test compound.

Reaction 1: $H_2O_2 + Cl^-$ in the presence of $MPO \rightarrow HOCl + H_2O$

Reaction 2: $HOCl + RNH_2 \rightarrow RNHCl + H_2O$

TMB may be used as the detector molecule. It is used at a final concentration of about 1 mM so that it is present at a vast excess over oxidant, which ensures a 1:1 stoichiometry for its reaction with taurine chloramine. The addition of potassium iodide is essential because it catalyses the reaction between taurine chloramine and TMB, and no reaction occurs in the absence of iodide (see Reactions 3 and 4, below). A pH of about 5.4 has been found to be optimal to maintain the stability of oxidized TMB and allow taurine chloramine to oxidize iodide. At a lower pH, non-specific oxidation of iodide can occur and at a higher pH, oxidation of iodide is slow and oxidized TMB is less stable.

Reaction 3: $RNHCl + I^- + H_2O + H^+ \rightarrow RNH_2 + HOI$

Reaction 4: $HOI + TMB \rightarrow TMB_{ox} + I^- + H_2O$

The taurine chloramine assay of the present invention comprises two parts, one, a process to generate taurine chloramine and, two, a process to oxidize a detector molecule such as TMB. In the first reaction, myeloperoxidase forms hypochlorous acid which is reacted with taurine to become trapped as taurine chloramine. In the second reaction, the formed taurine chloramine is used to quantitatively oxidise, for example, TMB to form oxidized TMB.

As a way of validating the above assay, taurine chloramine was generated by adding reagent HOCl to 5.5 mM taurine in 10 mM phosphate buffer pH 7.4 containing 140 mM sodium chloride. When an equal volume of developing reagent was added to the taurine chloramine the solution turned blue. The absorption spectrum of product has a broad peak between 500 and 700 nm with the maximum at 645 nm. The extinction coefficient was determined to be $14,520 \pm 330$ $M^{-1}$ $cm^{-1}$. The absorption at 645 nm was found to be directly proportional to the concentration of HOCl added to the PBST.

The optimal concentration of iodide was determined by employing a range of concentrations of iodide from 0 to 1 mM. Maximum formation of oxidized TMB was found to occur at iodide concentrations of greater than 10 μM.

It is known that DMSO interferes with the taurine chloramine assay when the oxidation of TMB is promoted by lowering the pH to 1. Therefore, inhibition of the oxidation of TMB by DMSO in the assay of the present invention was measured. To measure inhibition, a range of concentrations of DMSO was added to PBST (pH 7.4) before adding 56 μM HOCl. The reaction was permitted to proceed for 10 minutes before adding an equal volume of developing reagent. It was found that DMSO had only a minor effect on the detection of taurine chloramine provided that the concentration of DMSO was below about 1% in the PBST.

The taurine chloramine assay of the present invention was used to detect HOCl generated by purified human myeloperoxidase. Hydrogen peroxide (100 μM) was added to 20 mM phosphate buffer pH 6.5 containing 20 nM myeloperoxidase, 100 mM NaCl and 10 mM taurine. The mixture was incubated for 15 minutes at room temperature and the reaction stopped by adding catalase (10 μg/ml). Five minutes later developing reagent was added to detect the generated taurine chloramine. The amount of taurine chloramine produced was compared to that formed by adding 100 μM HOCl to the PBST. By comparison with the HOCl standard, it was shown that 100 μM hydrogen peroxide was converted into 113 μM HOCl. Therefore, within experimental error, all the hydrogen peroxide had been converted into HOCl and then trapped as taurine chloramine. The concentration of stock hydrogen peroxide was determined using $E_{240}$ 43.6 $M^{-1}$ $cm^{-1}$ and that of stock hypochlorite using $E_{292}$ 350 $M^{-1}$ $cm^{-1}$.

More particularly, the method of the present invention comprises:

Studies were performed to determine whether any oxidation of TMB occurs in the absence of chloride, in other words, to show that oxidation of TMB is limited to the original formation of HOCl, and it does not occur through direct oxidation by hydrogen peroxide and myeloperoxidase. Oxidation of TMB was not observed in the absence of chloride and further studies with catalase support this observation.

The ability of various compounds to affect the chlorination activity of myeloperoxidase confirmed that the assay of the present invention was measuring HOCl production, and that the assay is suitable for revealing potential inhibitors of the enzyme.

Hypochlorous acid was generated by myeloperoxidase in the absence or presence of 10 μM test compounds under the conditions described above for the time course experiment. Reactions were initiated by adding hydrogen peroxide and stopped five minutes later by adding catalase. Addition of catalase at 20 μg/ml achieved a 90% inhibition of the formation of HOCl.

All of the above assays may also optionally be run in the presence of tyrosine. A suitable concentration of tyrosine is about 5 to 20 μM.

A time course experiment showed that tyrosine enhanced production of HOCl because hydrogen peroxide was inhibiting myeloperoxidase. This experiment also showed that the chlorination activity of myeloperoxidase is being measured because tyrosine does not affect the peroxidation activity. This conclusion is supported by the effect of dapsone which is known to inhibit the chlorination activity but not the peroxidation activity of myeloperoxidase. Further experiments showed that dapsone, ABAH, p-bromoaniline, and dimethoxybenzene inhibited the production of HOCl to a similar extent as has been shown in other assays for the chlorination activity of myeloperoxidase. Thus, the assay of the present invention is suitable for revealing inhibitors of myeloperoxidase. Experiments also showed that DMSO did not affect the detection of HOCl. The results are presented in Table 1.

TABLE 1

Inhibitors of HOCl production by purified human myeloperoxidase.

| Inhibitor | [HOCl] (μM) | % Inhibition |
| --- | --- | --- |
| None | 56.2 ± 2.1 | 0 |
| Dapsone | 1.8 ± 0.1 | 97 |
| ABAH | 5.5 ± 1.1 | 90 |
| Tyrosine | 107.0 ± 0.5 | −90 |
| p-Bromoaniline | 2.5 ± 0.1 | 95.6 |
| 1,4-Dimethoxybenzene | 15.2 ± 1.0 | 73 |
| Catalase | 8.8 ± 1.3 | 84 |
| DMSO (0.1%) | 52.8 ± 1.2 | 6 |

In another aspect, the invention relates to the use of an assay method essentially as described above to measure MPO activity levels, particularly in biological fluids.

Myeloperoxidase activity has been implicated in numerous inflammatory diseases including Alzheimer's disease, multiple sclerosis, asthma, atherosclerosis, cancer, cystic fibrosis, chronic obstructive pulmonary disease, inflammatory bowel disease, and rheumatoid arthritis. The assay of the present invention may thus be used to look for MPO as a risk factor in a wide range of inflammatory diseases, including neuroinflammatory diseases.

Neutrophils and other phagocytes manufacture $O_2^-$ (superoxide) by the one-electron reduction of oxygen at the expense of NADPH. Most of the $O_2^-$ reacts with itself to form $H_2O_2$ (hydrogen peroxide). From these agents a large number of highly reactive microbicidal oxidants are formed, including HOCl (hypochlorous acid), which is produced by the myeloperoxidase-catalyzed oxidation of $Cl^-$ by $H_2O_2$; OH (hydroxyl radical), produced by the reduction of $H_2O_2$ by $Fe^{++}$ or $Cu^+$; $ONOO^-$ (peroxynitrite), formed by the reaction between $O_2^-$ and NO; and many others. These reactive oxidants are manufactured for the purpose of killing invading microorganisms, but they also inflict damage on nearby tissues, and are thought to be of pathogenic significance in a large number of diseases (B. M. Babior, Am. J. Med., 2000, 109, 33–44). Included among these are Alzheimer's disease, multiple sclerosis, asthma, atherosclerosis, cancer, cystic fibrosis, chronic obstructive pulmonary disease, inflammatory bowel disease, rheumatoid arthritis, emphysema, acute respiratory distress syndrome, reperfusion injury and malignancy.

MPO is also implicated in coronary artery disease (Hazen et al, JAMA, 2001, 286,2136–2142). Thus, the assay of the present invention may be used to look for MPO in peripheral blood neutrophils as a risk factor for atherosclerosis.

Assays for the identification of inhibitors of myeloperoxidase will be invaluable in demonstrating the contribution of hypochlorous acid to the pathogenesis of such diseases, as well as for diagnostic tools. They will also provide a platform for the development of effective drugs against myeloperoxidase-dependent tissue damage.

The invention is now illustrated by means of the following non-limiting examples.

EXAMPLE 1

Here we describe an in vitro MPO assay that was developed to assess inhibition of enzyme activity. Essentially the MPO assay was designed to measure the production of hypochlorous acid (HOCl), which is the key physiological product generated by the enzyme in vivo. An outline of the assay reactions is given:

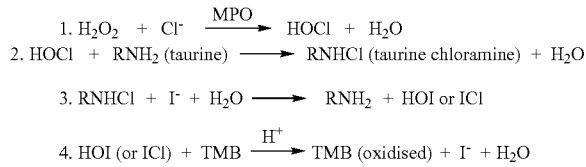

The reaction mixtures in 20 mM phosphate buffer pH 6.5 contained 2.5 nM MPO (purified human enzyme from Planta), 100 μM $H_2O_2$, 140 mM NaCl, 10 mM taurine, 20 μM tyrosine and compound solvent, DMSO, at 1%. Compounds were preincubated with the MPO enzyme in buffer for about 15 minutes prior to start of the reaction with $H_2O_2$. The whole reaction was carried out at room temperature for 10 minutes in a 96-well plate. The reaction was terminated by a stop/developing reagent, which consisted, in their final concentrations, of glacial acetic acid (400 mM), KI (100 μM) and TMB in dimethylformamide (10 mM). All test concentrations were done in duplicate with at least two separate determinations (n=2; unless otherwise stated). The inhibitory concentration for a compound is presented as $pIC_{50}$, which is $-\log IC_{50}$.

Various compounds have been tested against the human MPO. It can be seen that dapsone is the most potent inhibitor of the sulfones/sulfonamides tested. Indoles and other compounds are also effective in blocking the production of HOCl by human MPO. All data obtained for the sulfones/sulfonamides, indoles and miscellaneous compounds are presented in Tables 2, 3 and 4, respectively.

TABLE 2

Inhibition of human MPO-HOCl production by sulfones/sulfonamides

| Compound | $pIC_{50}$ |
|---|---|
| Dapsone | 6.2 |
| N-1(2-thiazolyl)-sulfanilamide | 6.0 |
| Sulfanilamide | 6.0 |
| Sulfapyridine | 5.7 |
| Sulfaguanidine | 5.5 |
| Sulfisoxazole | 5.2 |
| Sulfadiazine | 5.2 |
| Sulfanitran | 5.1 |

TABLE 3

Inhibition of human MPO-HOCl production by indoles

| Compound | $pIC_{50}$ |
|---|---|
| 5-Methoxytryptophol | 6.3 |
| 5-Methoxytryptamine | 6.2 |
| Melatonin | 6.1 |
| 3-Methylindole | 5.9 |
| 6-Methoxyindole | 5.8 |
| Indole | 5.7 |
| 5-Methoxyindole | 5.6 |

TABLE 4

Inhibition of human MPO-HOCl production by miscellaneous compounds

| Compound | $pIC_{50}$ |
|---|---|
| Ethyl aminobenzoate | 6.2 |
| 3-Aminobenzoic acid ethyl ester | 6.2 |
| p-Aminobenzamidine | 5.6 |
| Piroxicam | 5.6 (n = 1) |
| Diclofenac | 5.4 |
| Vanillin | 5.1 |

EXAMPLE 2

Here we describe the use of a functional human neutrophil assay to determine the effects of MPO inhibitors on the production of HOCl. This assay detects the production of HOCl from stimulated (e.g. PMA, LPS, fMLP, zymozan) human neutrophils. Human neutrophils were purified from fresh heparinised blood by density centrifugation on Polymorphprep (Nycomed). These neutrophils were used immediately after purification. A standard a reaction mixture contained the following: 2×106 neutrophils, 140 mM NaCl, 5 mM taurine, 0.5 mM $MgCl_2$, 1 mM $CaCl_2$ and 1 mg/ml glucose. Test compounds were made up in DMSO and added to cells, with a final DMSO concentration of 0.5%. Test compounds were given 15 minutes preincubation at 37° C. with neutrophils prior to the addition of the PMA stimulant (1 µg/ml). The assay was then allowed to progress for another 30 minutes at 37° C. At the end of the incubation, supernatants were collected by centrifugation and assayed for HOCl by using the stop/development reagent as above. All compounds were tested in duplicate with at least two separate determinations, n=2 from two different donors.

The data for some of these inhibitors are shown in Table 5.

TABLE 5

Inhibition of HOCl production by stimulated human neutrophils

| HOCl production by neutrophils | $pIC_{50}$ |
|---|---|
| Primaquine | 4.9 |
| Sufanilamide | 4.8 |
| Dapsone | 4.7 |
| Sulfapyridine | 4.5 |

We have also shown that under the assay conditions and concentrations of inhibitors used, human neutrophils were not affected by cytotoxicity, as assessed by the release of lactate dehydrogenase from damaged neutrophils. Lactate dehydrogenase activity was measured as described by Boehringer Mannheim GmbH, Sandhofer Strabe 116, D-68305 Mannheim, Germany (Cytotoxicity Detection Kit-LDH-Cat No: 1 644 793).

EXAMPLE 3

In this example, the assay is performed by reacting myeloperoxidase (5 to 20 nM) with hydrogen peroxide (100 µM) to generate hypochlorous acid in the presence of a potential myeloperoxidase inhibitor and reacting any formed hypochlorous acid with taurine to form taurine chloramine in 20 mM pH 6.5 phosphate buffer containing 100 mM sodium chloride and 10 mM taurine. Catalase is then added to a concentration of 20 µg/mL to destroy any residual hydrogen peroxide. An approximately equal volume of a developing reagent of 200 nM sodium acetate buffer pH 5.4 containing 2 mM TMB, 200 µM potassium iodide and 10 to 20% dimethylformamide is then added. The amount of oxidised 3,3',5,5'-tetramethylbenzidine formed is then measured after about 5 minutes using absorbance spectroscopy at about 645 nM.

EXAMPLE 4

An assay was run essentially as described in Example 3 except that:
myeloperoxidase (2.7 nM) was reacted with hydrogen peroxide (50 µM) in 20 mM phosphate buffer pH 6.5 containing 140 mM sodium chloride and 10 mM taurine in the presence of a potential myeloperoxidase inhibitor; this assay solution (150 µL) was then added to each well of a 96-well plate;
the reaction was stopped and developed by adding to each well 50 µL of a reagent comprising sodium iodide (100 µM), acetic acid (400 mM) and 10 mM TMB in 50% dimethylformamide; and
the amount of formed oxidised 3,3',5,5'-tetramethylbenzidine was measured.

The sensitivity and stability of the assay as described in Example 4 was established as follows. Varying concentrations of HOCl were added to 10 mM phosphate buffer containing 10 mM taurine to generate taurine chloramine. 150 µl of the solutions were added to 96 well plates followed by 50 µl of developing reagent. Plates were read ($A_{650}$) immediately after mixing and again at 1 hour to determine sensitivity and product stability. The results are shown in FIG. 2.

Figure 2:
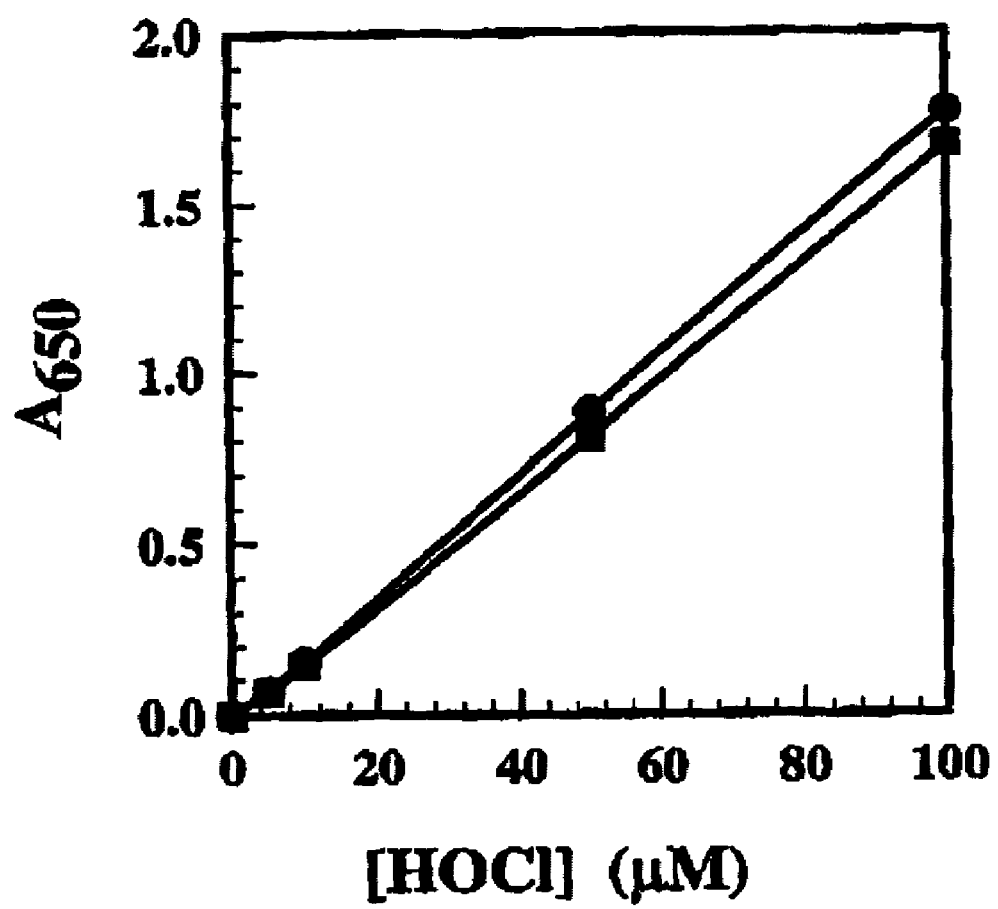

From FIG. 2 it can be seen that the TMB assay can easily detect 100 µM HOCl when performed in a 96-well plate. The product is very stable, with less than 10% decay at all concentrations after an hour at room temperature.

Figure 3:
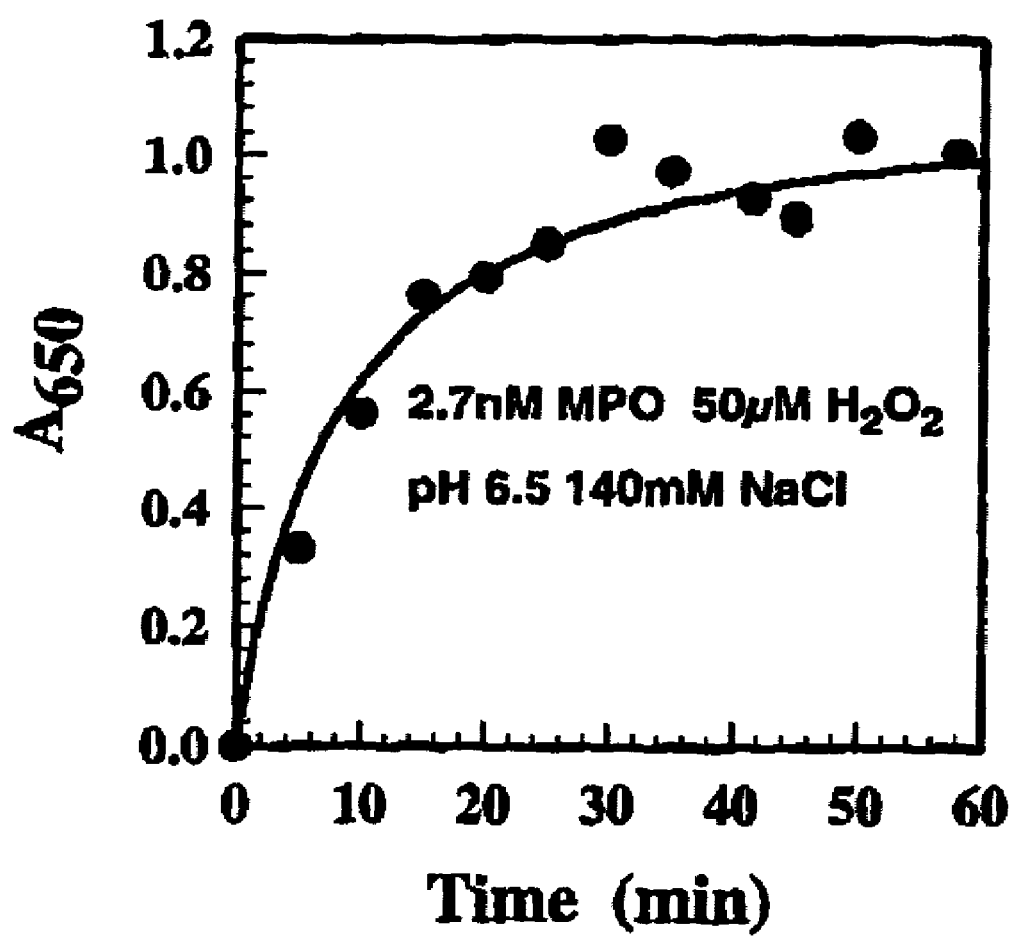

The time course for the production of HOCl by MPO is shown in FIG. 3:

From FIG. 3 it is apparent that conversion of $H_2O_2$ to HOCl took about 30 minutes under the reaction conditions described above. The shape of the progress curve indicates that there was little inhibition by $H_2O_2$. By comparing FIGS. 2 & 3 it is evident that MPO converted all the $H_2O_2$ into HOCl. There was thus no need to add any catalase to remove excess $H_2O_2$.

The colour yield for the reaction at 5 minutes increased by only 6% over the following hour. This indicates that addition of developing reagent prevents MPO from producing more HOCl and from directly oxidizing TMB.

EXAMPLE 5

Assay buffer: 20 mM sodium/potassium phosphate buffer pH 6.5 containing 10 mM taurine and 100 mM NaCl.

Developing reagent: 2 mM TMB, 200 µM KI, 200 mM acetate buffer pH 5.4 with 20% DMF.

To 10 µl of diluted compounds in assay buffer, 40 µl of MPO (final concentration 2.5 nM) was added for 10 minutes at room temperature. Then 50 µl of $H_2O_2$ (final concentration 100 µM), or assay buffer alone as a control, were added for 10 minutes at room temperature. The reaction was stopped by adding 10 µl 0.2 mg/ml of catalase (final concentration 18 µg/ml) for 5 minutes before 100 µl of TMB developing reagent was added (2 mM TMB in 200 mM acetate buffer pH 5.4 containing 20% dimethylformamide (DMF) and 200 µM KI). Plates were mixed and subsequently read at 650 nm.

Using the assay as described in Example 5, the reference compound dapsone showed an $IC_{50}$ value of 257±73 nM in the absence of tyrosine and 7120±610 nM in the presence of 8 µM tyrosine. A further reference compound, 4-aminobenzoic acid hydrazide (ABAH), showed an $IC_{50}$ value of 86±6 nM in the absence of tyrosine and 118±8 nM in the presence of 8 µM tyrosine.

EXAMPLE 6

This example describes an assay using dihydrorhodamine as the detector molecule that is suitable for high throughput screening (HTS) using 384 well plates.

Assay Construction—

| Enzyme solution | 110 ml of 200 mM $NaH_2PO_4$ pH 6.5 | (20 mM final) |
|---|---|---|
| | 110 ml of 1.4 M NaCl | (140 mM final) |
| | 110 ml of 100 mM Taurine | (10 mM final) |
| | 2.75 ml of 10 mM Tyrosine | (25 µM final) |
| | 275 µl of 10 µM MPO | (25 nM final) |
| | made up to 1100 ml distilled water | |

-continued

| Substrate solution | 110 ml of 200 mM NaH$_2$PO$_4$ pH 6.5 | (20 mM final) |
| --- | --- | --- |
| | 110 ml of 1.4 M NaCl | (140 mM final) |
| | 110 ml of 100 mM Taurine | (10 mM final) |
| | 20 µl of 8.8 M H$_2$O$_2$ | (160 µM final) |
| | made up to 1100 ml distilled water | |
| Detection solution | 110 ml of 200 mM NaH$_2$PO$_4$ pH 6.5 | (20 mM final) |
| | 110 ml of 1.4 M NaCl | (140 mM final) |
| | 110 ml of 100 mM Taurine | (10 mM final) |
| | 220 ml DMSO | (20% final) |
| | 16.5 ml of 20 mM Kl | (300 µM final) |
| | 8 ml of 72.5 mM Dihydrorhodamine | (527.3 µM final) |
| | made up to 1100 ml distilled water | |
| Negative control | 20 ml of 10 mM Dapsone | (1 mM final) |
| | made up to 200 ml distilled water | |

Compound dilutions are prepared using 5% DMSO/H$_2$O, to provide a compound concentration of 110 µM in 5 µl.

Positive and negative controls contain 0.4 µl DMSO vehicle and are diluted as with compound. Upon completion of the diluted plate, 5 µl of 1 mM of the reference compound dapsone was added to negative control wells.

Procedure

25 µl of the enzyme solution was added to all wells per plate;

the plates were then preincubated for 45 minutes;

25 µl of the substrate solution was added to all wells per plate;

the plates were then incubated for 15 minutes;

25 µl of the detection solution was added to all wells per plate; and the plates were counted by reading fluorescent intensity (excitation 485 nm, emission 530 nm, dichroic 505 nm).

EXAMPLE 7

Assay for Diagnostic Use

Assays of the MPO activity may also be performed on MPO containing tissue like blood, cellular fractions of blood, sputum or isolated tissue with an acute inflammation. For this type of assay it is preferred to use glucose oxidase to generate the hydrogen peroxide at about 10 µM/min and then stop the reaction after 5 to 10 minutes with the developing reagent. In this way the assay provides a simple diagnostic test and the information thus obtained can be widely used to assess MPO as a risk factor in numerous inflammatory diseases.

The invention claimed is:

1. A method for identifying inhibitors of myeloperoxidase (MPO), said method comprising:

reacting myeloperoxidase with hydrogen peroxide and a chloride source to generate hypochlorous acid in the presence of a potential inhibitor of said myeloperoxidase;

reacting any formed hypochlorous acid with an amine to form the corresponding chloramine;

optionally removing any unreacted hydrogen peroxide;

reacting any formed chloramine with a detector compound in the presence of iodide to form oxidised detector compound;

determining the amount of formed oxidised detector compound by measuring the absorbance or fluorescence at a wavelength;

identifying as inhibitors of myeloperoxidase those compounds which cause the amount of formed oxidised detector compound to be decreased.

2. The method according to claim 1 wherein the detector molecule is 3,3',5,5'-tetramethylbenzidine (TMB).

3. The method according to claim 1 or claim 2 wherein the amine is taurine.

4. The method according to claim 3 wherein the reaction of 3,3',5,5'-tetramethylbenzidine (TMB) with the taurine chloramine in the presence of iodide is conducted at about pH 5.4.

5. The method according to claim 1 wherein any unreacted hydrogen peroxide is removed using catalase.

6. The method according to claim 1 that is performed as a high throughput screen.

* * * * *